(12) United States Patent
Sawai et al.

(10) Patent No.: US 6,546,808 B2
(45) Date of Patent: Apr. 15, 2003

(54) METHOD OF EVALUATING HIGH FATIGUE STRENGTH MATERIAL IN HIGH TENSILE STRENGTH STEEL AND CREATION OF HIGH FATIGUE STRENGTH MATERIAL

(75) Inventors: Tatsuaki Sawai, Ibaraki (JP); Saburo Matsuoka, Ibaraki (JP); Takayuki Abe, Ibaraki (JP); Etsuo Takeuchi, Ibaraki (JP); Kensuke Miyahara, Ibaraki (JP); Hisashi Hirukawa, Ibaraki (JP); Kaneaki Tsuzaki, Ibaraki (JP); Yuji Kimura, Ibaraki (JP)

(73) Assignee: National Institute for Materials Science, Ibaraki (JP)

( * ) Notice: Subject to any disclaimer, the term of this patent is extended or adjusted under 35 U.S.C. 154(b) by 0 days.

(21) Appl. No.: 09/917,733

(22) Filed: Jul. 31, 2001

(65) Prior Publication Data

US 2002/0033053 A1 Mar. 21, 2002

(30) Foreign Application Priority Data

Jul. 31, 2000 (JP) ........................................ 2000-232531

(51) Int. Cl.$^7$ ................................................. G01N 3/32
(52) U.S. Cl. ........................................... 73/808; 73/799
(58) Field of Search ........................ 73/808, 643, 779, 73/851, 799; 148/127; 524/59

(56) References Cited

U.S. PATENT DOCUMENTS

| | | | | |
|---|---|---|---|---|
| 4,222,793 A | * | 9/1980 | Grindahl | 148/544 |
| 4,388,379 A | * | 6/1983 | Klingenmaier | 428/613 |
| 5,080,732 A | * | 1/1992 | Lacy et al. | 148/127 |
| 5,171,404 A | * | 12/1992 | Ellis et al. | 162/206 |
| 5,808,202 A | * | 9/1998 | Passarelli, Jr. | 73/643 |
| 6,305,229 B1 | * | 10/2001 | Inoue | 73/779 |

* cited by examiner

Primary Examiner—Max Noori
(74) Attorney, Agent, or Firm—Wenderoth, Lind & Ponack, L.L.P.

(57) ABSTRACT

The present invention provides a method of designing a high fatigue strength in high tensile strength steel, comprising: obtaining values of tensile strength $\sigma_B$ (unit thereof is MPa) and Vickers hardness Hv of the steel; measuring a flaw area of an inclusion, when a fracture origin is located only at a surface of the steel; and estimating, in designing the high fatigue strength steel, that a fatigue limit $\sigma_w$ (unit thereof is MPa) of the steel satisfies either $\sigma_w \geq 0.5\, \sigma_B$ or $\sigma_w \geq 1.6\, Hv$, when a square root of the flaw area, $(area)^{1/2}$ (unit thereof is m), contained in the steel is no larger than $45.8/\sigma_B^2$ or $4.47/Hv^2$. According to the present invention, a method of evaluating high fatigue strength in high tensile strength steel, in which method a relationship between a flaw dimension (area) of ODA and the fatigue strength is considered, and a high fatigue strength material can be provided.

23 Claims, 12 Drawing Sheets

Al₂O₃ type inclusion (SUP12 Heat A)

Matrix crack (SUP12 Heat D)

Duplex inclusion (Al,Mg,Ca,Si)

Quenched & tempered steel

Ausformed & tempered steel

Quenched & tempered steel (10 μm × 10 μm)

Ausformed & tempered steel (10 μm × 10 μm)

METHOD OF EVALUATING HIGH FATIGUE STRENGTH MATERIAL IN HIGH TENSILE STRENGTH STEEL AND CREATION OF HIGH FATIGUE STRENGTH MATERIAL

BACKGROUND OF THE INVENTION

1. Field of the Invention

The present invention relates to a method of evaluating high fatigue strength in high tensile strength steel, and creation of a high fatigue strength steel produced in accordance with the aforementioned evaluation method. More specifically, the present invention relates to a method of evaluating high fatigue strength in high tensile strength steel and creation of a high fatigue strength steel, which are useful for material designing and production of high tensile strength steel having high strength of giga-cycle fatigue. The high tensile strength steel having high giga-cycle fatigue strength is advantageously used for reducing weight and size of vehicle parts and others.

2. Description of the Related Art

High tensile strength steel having excellently high strength of giga-cycle fatigue has been on demand, in order to reduce weight and size of vehicle parts and others. However, in the case of high tensile strength steel of 1200-MPa-plus grade, fatigue strength saturates or rather decreases at the giga-cycle range, since internal fracture; that is, a fish eye-type fracture initiates at inclusions or internal facets. Therefore, it is not technologically easy to produce high tensile strength steel having high fatigue strength. Further, a method of designing high tensile strength steel having higher fatigue strength is hardly known, because a mechanism of the internal fracture is quite complicated.

An example of a method of designing high tensile strength steel includes the steps of: measuring size (area) and/or properties of flaws of the inclusion and internal facet; and calculating a fatigue limit from a correlation equation which defines a relationship between the flaw area and the fatigue limit.

However, as this method calculates only an approximate fatigue limit value by simplifying the complicated mechanism of the internal fracture, the method is by no means a designing method for high tensile strength steel having a higher fatigue strength.

A new attempt has been made in recent years, as one method of solving the complicated mechanism of the internal fracture, in which an optically dark area (ODA), which is presumably the fracture area developed by hydrogen around the inclusion, prior austenite grain boundary, dislocation and others, is observed and the relationship between the ODA (flaw area) and fatigue strength is analyzed. If the formation mechanism of ODA (flaw area) is made clear in the future, this discovery may contribute to providing a method of designing high tensile strength steel having excellent fatigue strength. However, this discovery has not yet been fully made and there does not exist a clear prospect of specifically designing such a method.

The invention of the present application has been achieved in consideration of the aforementioned problems of the prior art. The present invention has as an object providing a method of evaluating high fatigue strength in high tensile strength steel, and a high fatigue strength steel itself, in which method the relationship between the flaw size (area) of ODA and the fatigue strength is considered.

SUMMARY OF THE INVENTION

In order to solve the aforementioned problems, the present invention proposes, as a first aspect, a method of evaluating a high fatigue strength in high tensile strength steel, comprising the steps of obtaining values of tensile strength $\sigma_B$ (the unit thereof is MPa) and Vickers hardness Hv of the steel; and estimating, in designing the high fatigue strength steel, that the fatigue strength $\sigma_w$ (the unit thereof is MPa) of the steel satisfies either $\sigma_w \geq 0.5\,\sigma_B$ or $\sigma_w \geq 1.6\,\text{Hv}$, when a fracture origin is located only at a surface of the steel and a square root of the flaw area, $(\text{area})^{1/2}$ (the unit thereof is m), contained in the steel is no larger than $45.8/\sigma_B^2$ or $4.47/\text{Hv}^2$.

The present invention proposes, as a second aspect, a method of evaluating a high fatigue strength in high tensile strength steel, comprising the steps of: obtaining values of tensile strength $\sigma_B$ (the unit thereof is MPa) and Vickers hardness Hv of the steel; measuring flaw area of an inclusion, when a fracture origin is located inside the steel; and estimating, in designing high fatigue strength, that the fatigue limit $\sigma_w$ (the unit thereof is MPa) of the steel satisfies a condition that $\sigma_w \geq 3.38\,(\text{area}_i)^{-1/4}$.

The present invention propose, as a third aspect, a method of evaluating a high tensile strength structure, which method enables evaluation of high fatigue strength according to the aforementioned first or second aspects, which method comprises the steps of: measuring a maximum inhomogeneous structure area, $(\text{area}_{max,m})$, when the structure has been made homogeneous (i.e., the size of the inhomogeneous structure has been made small) or the structure has been made minute (i.e., a block width thereof has been reduced); setting a distribution of the maximum-minimum range of the maximum inhomogeneous structure area, $(\text{area}_{max,m})^{1/2}$, (the unit thereof is $\mu$m) within the range defined by the line: $(\text{area}_{max,m})^{1/2}=0$ and the line: $(\text{area}_{max,m})^{1/2}=0.9403y+4.571$ (y is a standardizing parameter, and a test standard area $S_O=6.2\times10^{-9}\,\text{m}^2$); and setting a distribution of the maximum-minimum range of the maximum block width $d_{max}$ (the unit thereof is $\mu$m) within the range defined by the line: $d_{max}=0$ and the line: $d_{max}=0.217y+0.701$ (y is a standardizing parameter, and a test standard area is $1\times10^{-10}\,\text{m}^2$).

The present invention proposes, as a fourth aspect, a method of producing a high fatigue strength steel, which method comprises producing steel according to the method of evaluating a high fatigue strength in high tensile strength steel of the aforementioned first and second aspects, and the method of evaluating a high tensile strength structure of the aforementioned third aspect.

The present invention proposes, as a fifth aspect, a method of producing a high fatigue strength, which method comprises producing steel according to the method of the aforementioned first aspect, by subjecting steel to a heat treatment for tempering the steel in a high vacuum of at least $2\times10^{-6}$ Pa.

Further, the present invention proposes, as a sixth aspect, a high fatigue strength material produced according to the method of evaluating a high fatigue strength in high tensile strength steel of the aforementioned first and second aspects, and the method of evaluating a high tensile strength structure of the aforementioned third aspect.

DETAILED DESCRIPTION OF THE PREFERRED EMBODIMENTS

Figure 1:
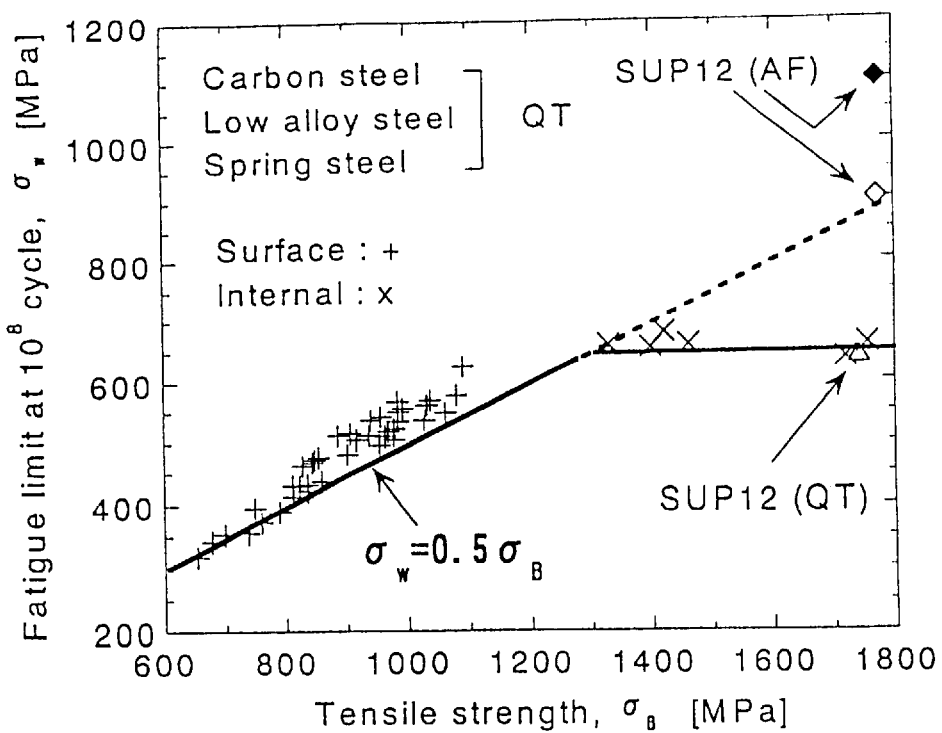
FIGS. 1(a)–1(b) are diagrams which show the relationship between the static strength (tensile strength and Vicker's hardness) and the fatigue limit at $10^9$ cycles in an embodiment of the present invention.

The invention of the present application has the features as described above. An embodiment of the present invention will be described hereinafter.

The present invention is significantly characteristic in that it proposes a method comprising the steps of: analyzing a correlation between fatigue strength and flaw area of inclusion (including an optically dark area (ODA)); and determining the flaw area, normally for the following three cases of: a) the case in which fracture origin is located only at a surface; b) the case in which fracture origin is located inside steel; and c) the case in which structure has been made homogeneous or grain thereof has been made minute; and thereby calculating fatigue limit.

Accordingly, in the present invention, as the correlation between the fatigue strength and the area of inclusion is made obvious, inclusion of desired size can be reliably provided, whereby high tensile strength steel having the same static strength but a higher fatigue strength, as compared with conventional high tensile strength steel, can be produced and designing fatigue strength of high tensile strength steel can be more reliably carried out.

In the present invention, the flaw area of inclusion represents the square root of the flaw area in cross section, which surface is normal to a load applying direction, of the inclusion, and has a length unit in terms of dimension. The area of a maximum inhomogeneous structure represents the square root of the maximum value of the inhomogeneous structure area in cross section, which surface is normal to a load applying direction, of the inhomogeneous structure, and has a length unit in terms of dimension.

Further, the present invention enables providing high tensile strength steel, which is produced by the aforementioned method of designing a high fatigue strength. Specifically, the present invention provides high tensile strength steel having the fatigue strength as defined below.

$\sigma_w \geq 0.5\sigma_B$ or $\sigma_w$ 1.6 HV, wherein $\sigma_B$ is tensile strength (the unit thereof is MPa), Hv is Vickers hardness, and $\sigma_w$ is fatigue limit (the unit thereof is MPa). It should be noted that high tensile strength steel having such excellent fatigue strength as described above has not been available up to now.

First, in steel having known tensile strength $\sigma_B$ (MPa) and Vickers hardness Hv, and specifically, in steel in which fracture origin is located only at the surface thereof (in other words, in steel in which surface fracture occurs prior to internal fracture) (the aforementioned case a)), the method of obtaining the fatigue limit $\sigma_w$ will be described.

In this case, as the fracture origin is located only at the surface of the steel, it is assumed that the steel is high tensile strength steel which does not experience generation of an optically dark area (ODA) in which the fatigue limit of the surface fracture, $O_{w, surface}$, exceeds $0.5\sigma_B$ or 1.6 Hv. The maximum value of the flaw area in which surface fracture occurs prior to the internal fracture (the maximum flaw), (area)$^{1/2}_{max}$ (the unit thereof is m) can be expressed as follows, as a specific case of (the square root of) the flaw area (the unit thereof is m), by using the fatigue limit $\sigma_{w,surface}$ of the surface fracture.

Equation (1)

$$\frac{(\sqrt{area})_{max}}{\sqrt{\pi}} = \frac{1}{\pi}\left(\frac{\Delta K_{th}}{0.666\sigma_{w, surface}}\right)^2 \quad (1)$$

Here, $\Delta K_{th}$ is a lower limit value of a stress intensity factor, that is, fatigue threshold, spreading coefficient range in which cracking proceeds. The general value thereof is 3 MPam$^{1/2}$, approximately. Accordingly, the maximum flaw area, (area)$^{1/2}_{max}$, is expressed as follows, by using tensile strength $S_B$ (the unit thereof is MPa) and Vickers hardness Hv.

Equation (2)

$$(\sqrt{area})_{max} = 45.8/\sigma_B^2 \text{ or } (\sqrt{area})_{max} = 4.47/Hv^2 \quad (2)$$

From the aforementioned equation (2), it is understood that, when the fracture origin is located only at the surface of steel and if the flaw dimension area, (area)$^{1/2}$, is no larger than $45.8/\sigma_B^2$ or $4.47/Hv^2$, the fatigue limit $\sigma_w$ of the steel satisfies either $\sigma_w \geq 0.5\sigma_B$ or $\sigma_w \geq 1.6$ Hv. In other words, by designing a high fatigue strength steel such that the material satisfies the aforementioned conditions, high tensile strength steel whose fatigue limit $\sigma_w$ satisfies either $\sigma_w \geq 0.5\sigma_B$ or $\sigma_w \geq 1.6$ Hv can be produced.

Next, in steel in which the fracture origin is located inside the steel (the aforementioned case b)), the method of obtaining the fatigue limit $\sigma_w$ will be described. When the flaw area of inclusion is expressed as area$_i$ (the unit of (area$_i$)$^{1/2}$ is m), since the fatigue limit at the internal fracture origin is preferentially dealt with, the fatigue limit $\sigma_w$ expressed as follows.

Equation (3)

$$\sigma_w = \frac{\Delta K_{th}}{0.666 \cdot \sqrt{\sqrt{\pi} \cdot \sqrt{area_i}}} \quad (3)$$

Here, when. $\Delta K_{th}$ is 3 Mpa.m$^{1/2}$, $\sigma_w$ is expressed as follows.

Equation (4)

$$\sigma_w = 3.38(\text{area}_i)^{-1/4} \quad (4)$$

That is, it is understood that, in steel in which ODA is not generated and the inclusion area is not under control, the fatigue limit $\sigma_w$ of the steel has a value of $3.38\,(\text{area}_i)^{-1/4}$ or larger ($\text{area}_i$ is the measured flaw area of inclusion). In other words, by designing a high fatigue strength steel such that the steel satisfies the aforementioned conditions, high tensile strength steel whose fatigue limit $\sigma_w$ satisfies $\sigma_w \geq 3.38\,(\text{area}_i)^{-1/4}$ can be obtained.

Next, the aforementioned case c) in which structure has been made homogeneous (i.e., the size of inhomogeneous structure has been made small) or the structure has been made minute (i.e., block width thereof has been reduced) will be described as the method of evaluating high tensile strength structure, which method enables designing a high fatigue strength material as described in the aforementioned a) and b).

Specifically, in the case of c), when the maximum inhomogeneous structure area, $\text{area}_{max,m}$, is measured, distribution of the maximum-minimum range of the maximum inhomogeneous structure area, $(\text{area}_{max,m})^{1/2}$ is to be within the range defined by the line: $(\text{area}_{max,m})^{1/2}=0$ and the line: $(\text{area}_{max,m})^{1/2}=0.9403y+4.571$, and the distribution of the maximum-minimum range of maximum block width $d_{max}$ is to be within the range defined by the line: $d_{max}=0$ and the line: $d_{max}=0.217y+0.701$. Here, a test standard area $S_O$ for obtaining the maximum inhomogeneous structure area, $(\text{area}_m)^{1/2}$, is preferably about $6.2 \times 10^{-9}\,\text{m}^2$, and a test standard area for obtaining the maximum block width $d_{max}$ is preferably about $1 \times 10^{-10}\,\text{m}^2$.

The present invention will be described further in detail hereinafter, by the following examples.

EXAMPLES

Example 1

<A> Preparation of Samples and Pre-treatment

In order to demonstrate precision of the method of evaluating a high fatigue strength of the present invention, an example was actually carried out by using spring steel SUP12 and valve spring steel SWOSC-V. First, samples of these types of steel were prepared and pre-treated. Thereafter, the mechanical properties of the samples were examined.

The chemical components of spring steel SUP12 and valve spring steel SWOSC-V are shown in Table 1. Six different heats of samples including four different heats of spring steel SUP12 (heat A, heat B2, heat C1, heat D1) and two different heats of valve spring steel SWOSC-V (heat E2, heat F) were prepared, according to the types of heat. Product form, conditions of a heating treatment, tensile strength $\sigma_B$ and Vickers hardness Hv of the steel samples are shown in Table 2. For the heat D1 of spring steel SUP12, two types of samples which differ from each other in conditions of the heating treatment i.e., a normally-quenched-and-tempered material (a QT material) and a modified ausform material (an AF material) were prepared.

TABLE 1

| Types of Steel | Heat | Chemical Component (mass %) | | | | | | | | |
|---|---|---|---|---|---|---|---|---|---|---|
| | | C | Si | Mn | P | S | Cu | Ni | Cr | Al |
| SUP12 | A | 0.53 | 1.49 | 0.69 | 0.011 | 0.007 | 0.01 | 0.02 | 0.74 | 0.039 |
| | B2 | 0.56 | 1.50 | 0.67 | 0.014 | 0.008 | 0.01 | 0.01 | 0.72 | 0.021 |
| | C1 | 0.56 | 1.48 | 0.72 | 0.012 | 0.009 | — | — | 0.71 | 0.001 |
| | D1 | 0.57 | 1.48 | 0.72 | 0.008 | 0.007 | — | — | 0.73 | 0.005 |
| SWOSC-V | E2 | 0.57 | 1.46 | 0.63 | 0.008 | 0.006 | 0.01 | 0.01 | 0.68 | 0.001 |
| | F | 0.58 | 1.44 | 0.70 | 0.013 | 0.006 | 0.01 | 0.02 | 0.70 | 0.001 |

TABLE 2

Product form, Conditions of heating treatment, Tensile strength and Vickers hardness

| Type of Steel | Heat | Product form | Conditions of heating treatment | Tensile strength (MPa) | Vickers hardness HV (196N) | Note |
|---|---|---|---|---|---|---|
| SUP12 | A | Round Rod φ 21 mm | Quenching at 845° C. × 30 minutes, oil cooling Temperature at 430° C. = 60 minutes, water cooling | 1720 | 516 | OT material |
| | B2 | Billet: 160 × 160 mm | | — | 530 | |
| | C1 | Round Rod φ 20 mm | | — | 511 | |
| | D1 | Round Rod φ 20 mm | | 1742 | 518 | |
| SWOSC-V | E2 | Billet: 160 × 160 mm | | — | 532 | |
| | F | Wire material φ 11 mm | | — | 528 | |

TABLE 2-continued

Product form, Conditions of heating treatment, Tensile strength and Vickers hardness

| Type of Steel | Heat | Product form | Conditions of heating treatment | Tensile strength (MPa) | Vickers hardness HV (196N) | Note |
|---|---|---|---|---|---|---|
| SUP12 | D1 | Round Rod φ 50 mm | Modified ausforming at 845° C. = 30 minutes, air cooling, 800° C., 50% water cooling Tempering at 430° C. = 60 minutes, water cooling | 1770 | 534 | AF material |

First, for each type of the six types of steel described above, a graph of the maximum-minimum range was statistically prepared for obtaining the maximum flaw area, (area$_{max, m}$)$^{1/2}$. In the present example, the flaw area of the maximum inclusion can be reliably employed when fracture does not occur inside the steel but is located only at the surface of the steel.

Figure 1B:
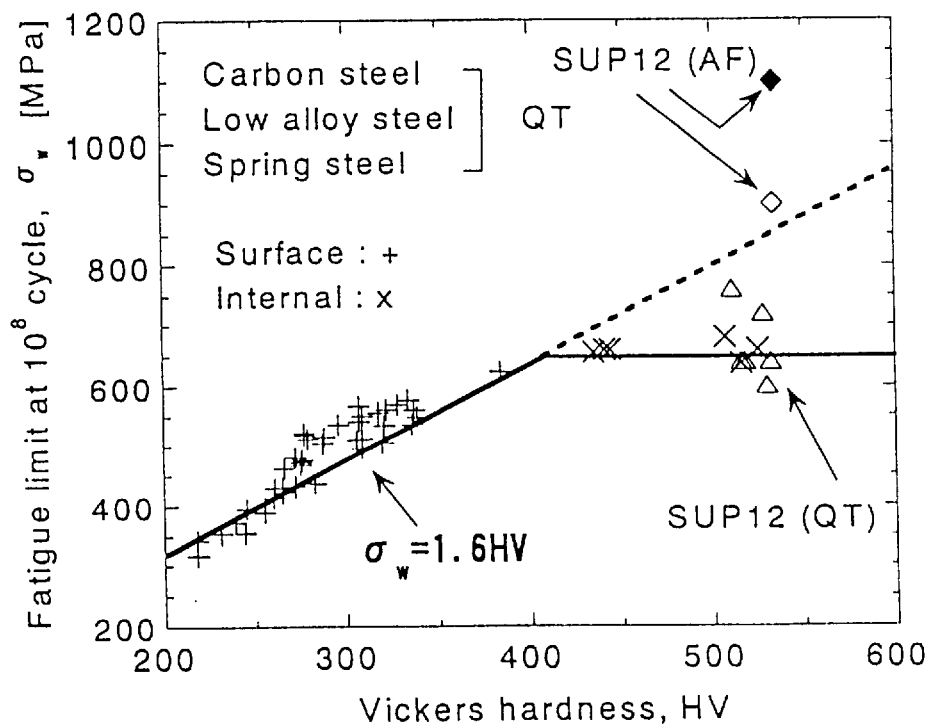

By using the statistical graph of the maximum-minimum range, the maximum flaw area, (area$_{max, m}$)$^{1/2}$, was obtained at the test standard area $S_O$ of 0.482 mm². This procedure of obtaining (area$_{max,m}$)$^{1/2}$ was repeated twenty times at different sites, whereby a distribution line of the maximum inclusion was obtained. On the basis of the obtained distribution line, the maximum flaw area, (area$_{max, m}$)$^{1/2}$, which was present in the minimum broken-flaw area ($\pi r^2 = \pi \times 6^2$ = 28.3 mm², r represents radius) of the fatigue test specimen was obtained. The result is shown in Table 3.

cycles fatigue limit is shown in FIG. 1(a). The relationship between Vickers hardness Hv and the 10⁸-cycles fatigue limit, is shown in FIG. 1(b). These figures show a surface fracture symbol ♦ and an internal fracture symbol ◊ of the AF material of SUP12 steel, as well as an internal fracture symbol Δ of the QT material of SUP12 steel. In FIGS. 1(a) and 1(b), the 10⁸-cycles fatigue limit obtained from FIG. 11 and FIG. 12 described below is indicated by using the symbol ♦ and the symbol ◊. In addition, in FIGS. 1(a) and 1(b), the surface fracture was indicated by the symbol+ and internal fracture was indicated by the symbol× for carbon steels, low alloy steels, and spring steels, as well. The result of the internal fracture of these steels (indicated by the symbol× in the figures) shows that the fracture origin is the Al$_2$O$_3$-based inclusion. In the low tensile strength steel (indicated by the symbol+), the relationship: $\sigma_w = 0.5\, \sigma_B$ is observed. However, in the high tensile strength steel (indicated by the symbol×), no correlation between the tensile strength and the fatigue limit is observed.

TABLE 3

Results of Inclusion Test

| Type of Steel | Heat | Symbol representing Heating Treatment | Type of Inclusion | √area$_{max}$ (μm) 28.3 mm² | EPMA Analysis Component | Type of inclusion |
|---|---|---|---|---|---|---|
| SUP12 | A | QT | D | 15 | Al | Al$_2$O$_3$ |
|  |  |  | D (Ti) |  | Ti > Zr > N | TiN.ZrN |
|  | B2 |  | D | 18 | Al > Ca > Mg > Si | Al$_2$O$_3$.CaO.MgO.SiO$_2$ |
|  |  |  | D (Ti) |  | Ti > V > Zr, N | TiN.VN.ZrN |
|  | C1 |  | D | 12 | Si > Ca > Al > Mn | SiO$_1$.CaO.Al$_2$O$_3$.MnO.MgO |
|  |  |  | D (Ti) |  | Ti > V > Zr | TiN.VN.ZrN |
| SWOSC-V | E2 |  | D | 11 | Si > Ca > Mg > Al > Mn > Zr | SiO$_1$.CaO.MgO.Al$_2$O$_3$.ZrO$_3$ |
|  | F |  | D | 11 | Si > Ca > Zr > Al | SiO$_2$.CaO.MgO.Al$_2$O$_3$.ZrO$_3$ |
| SUP12 | D1 | AF | D | 6 5 14 | Al > Mg | Al$_2$O$_3$.MgO |

From Table 3, it is understood that the inclusion which exhibits the (area$_{max, m}$)$^{1/2}$ of 15 μm is an Al$_2$O$_3$-base inclusion, in Heat A of the SUP12 Steel. However, from Table 3, it is also understood that, in the other three types of SUP12 steel (Heats B2, C1 and D1) and two types of SWOSC-V steel (Heats E2 and F), inclusions are an Al$_2$O$_3$-based composite inclusion or an SiO$_2$-based composite inclusion. The latter results indicate that advanced inclusion-softening control has been carried out therein.

The relationship between tensile strength $\sigma_B$ of high tensile strength steel of 1200-MPa-plus grade (the present invention is directed to the steel of this type) and a 10⁸-

From FIGS. 1(a) and 1(b), it is understood that, in the AF material (indicated by the symbols ♦ and ◊), $\sigma_w$ exceeds 0.5 $\sigma_B$ or $\sigma_w$ exceeds 1.6 Hv even if the internal fracture has occurred therein. Accordingly, it can be concluded that steel having excellently high fatigue strength can be designed according to the method of evaluating a high fatigue strength material of the present invention.

Figure 2:
FIGS. 2(a)–2(c) are scanning electron microscope (SEM) photographs of an internal fracture origin and vicinities thereof.
Figure 3:
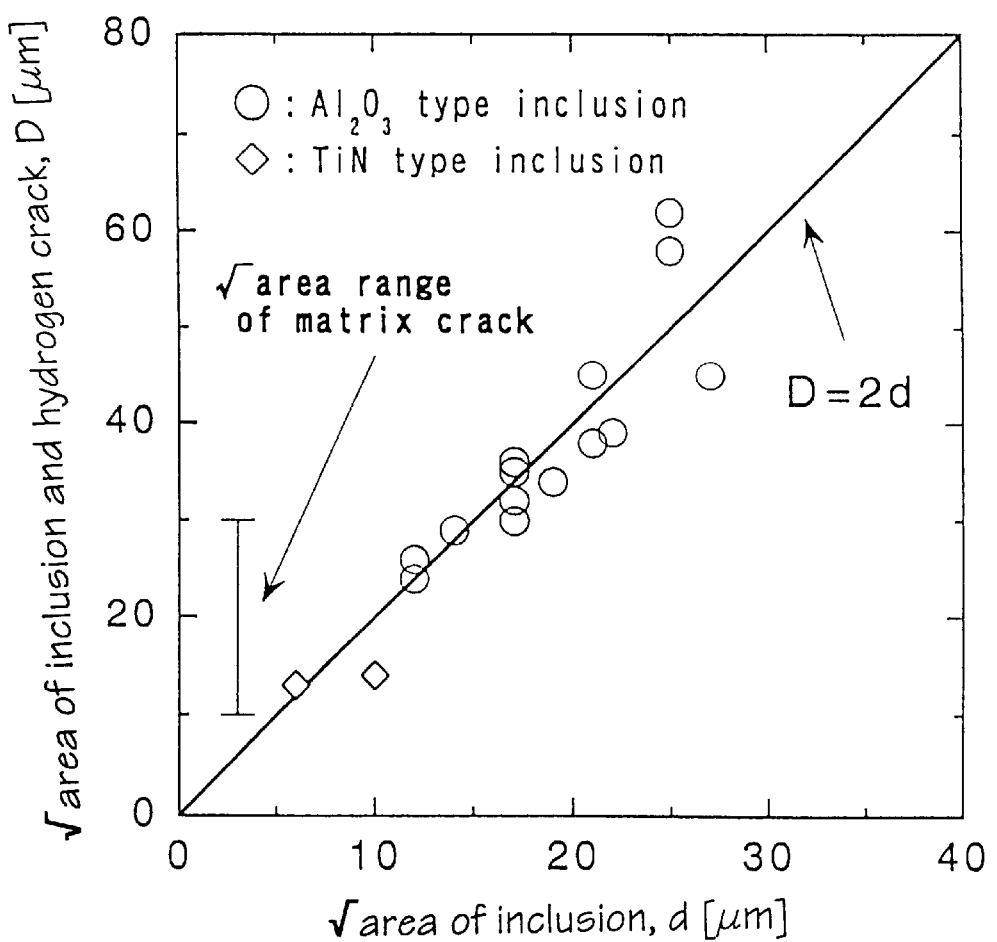
FIG. 3 is a diagram which shows the relationship between an optically dark area (ODA) and a flaw area of an inclusion, (area)$^{1/2}$ in the embodiment of the present invention.

<B> Method of Evaluating a High Fatigue Strength Material in which the Internal Fracture Origin is Considered In recent years, it has been known that the optically dark are (ODA) is formed around an inclusion before the generation of ordinary fatigue cracks, which ODA is observed as the rough surface in an SEM (scanning electron microscope) photograph of the inclusion and vicinities thereof (refer to FIG. 2(a) which is a SEM photograph of the internal fracture origin and the vicinities thereof), and such an ODA increases the effective flaw area of the inclusion. Therefore, the present example considered this point, as well. Specifically, as a result of analyzing the high tensile strength steel on which the fatigue test had been carried out, it was discovered that there is a correlation, as shown in FIG. 3, between the flaw area of the inclusion and ODA (i.e., D=2d).

Figure 4:
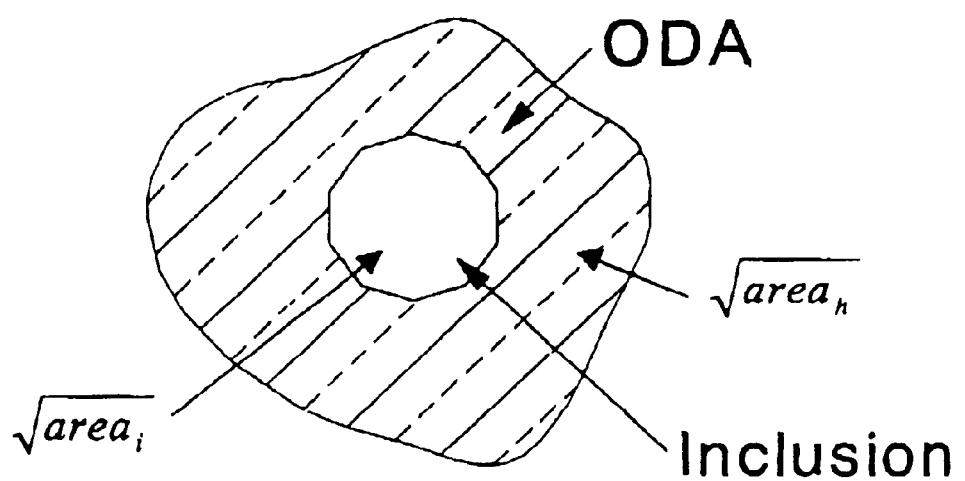
FIG. 4 is a schematic diagram which illustrates an origin of an internal fracture.

Here, "D" is expressed by the vertical axis and represents the entire flaw area, $(area_h)^{1/2}$, that includes the flaw area of the ODA resulting from the inclusion-originated internal fracture, as well. On the other hand, "d" is expressed by the horizontal axis and represents the flaw area, $(area_i)^{1/2}$, that is of the case in which the fracture origin is located inside the steel (i.e., the case in which there is no influence of ODA) and constituted of only of the inclusion. This state is schematically shown in FIG. 4.

Figure 5:
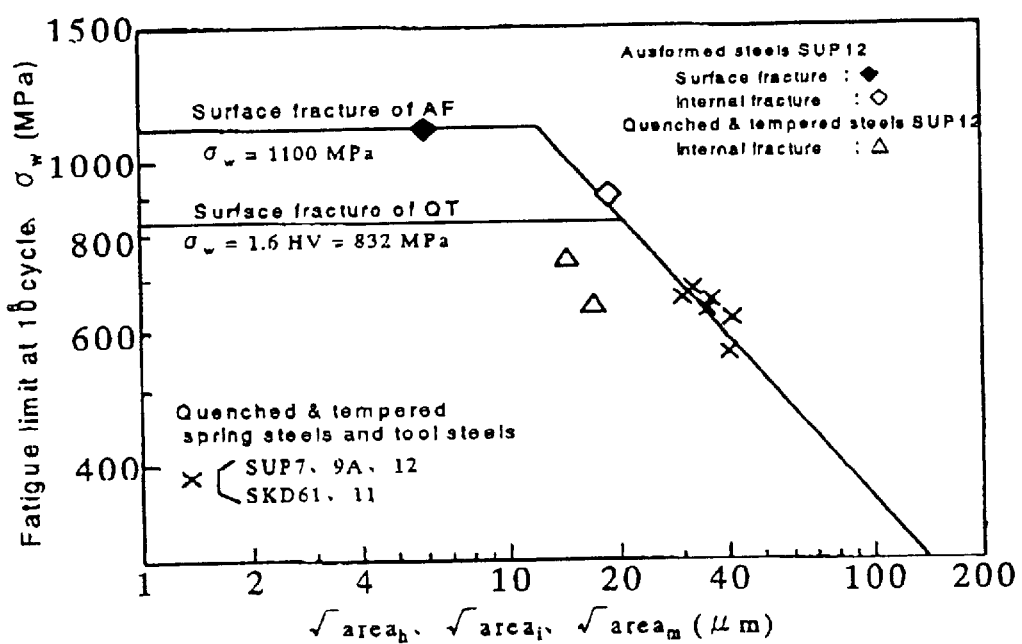
FIG. 5 is a diagram which shows the relationship between the flaw area, (area)$^{1/2}$, and fatigue limit in the embodiment of the present invention.

On the basis of the aforementioned findings, the relationship between the fatigue limit $\sigma_w$ and the flaw area, $(area)^{1/2}$, has been arranged as shown in FIG. 5. In FIG. 5, the $10^8$-cycles fatigue limit obtained from FIG. 11 and FIG. 12 described below is indicated by the symbol ♦ and the symbol ◊. The flaw area of the surface fracture (the symbol ♦) is based on the assumption that the maximum inhomogeneous structure area, $(area_{max,m})^{1/2}$, of the D1 Heat AF material of Table 3 can take the value of 5 μm. Here, as the flaw area, $(area)^{1/2}$, of the horizontal axis the entire flaw area, $(area_h)^{1/2}$, that includes the ODA in the case in which the inclusion-originated internal fracture occurs; the flaw area, $(area_i)^{1/2}$, that is constituted of only the inclusion in the case in which the flaw area of inclusion is not under control; and the flaw area, $(area_{max,m})^{1/2}$, in the case in which a structure crack-originated internal fracture occurs, are each employed. The line in FIG. 5, which represents the aforementioned correlation, can be expressed as follows.

Equation (5)

$$\sigma_w = \frac{\Delta K_{th}}{0.666 \cdot \sqrt{\sqrt{\pi} \cdot \sqrt{area}}} = 3.38(area)^{-1/4} \quad (5)$$

Here, the line represents the correlation when $\Delta K_{th}$ is 3 MPam$^{1/2}$. Another line is obtained when the fatigue limit of the surface fracture $\sigma_w$ satisfies either $\sigma_w \geq 0.5\ \sigma_B$ or $\sigma_w \geq 1.6$ Hv. From the intersection of these lines, the maximum flaw area, $(area)^{1/2}_{max}$, can be expressed as follows.

Equation (6)

$$(\sqrt{area})_{max} = 45.8/\sigma_B^2 \text{ or } (\sqrt{area})_{max} = 4.47/Hv^2 \quad (6)$$

From equation (6), it is understood that, in the present invention, by setting the flaw area at a value which is no larger than the lower limit, the fatigue limit of the resulting high tensile strength steel becomes no less than 0.5 times as much as the tensile strength or no less than 1.6 times as much as the Vickers hardness.

<C> The Case in which the Inclusion Flaw Area is not Under Control

Figure 2B:
Figure 2C:
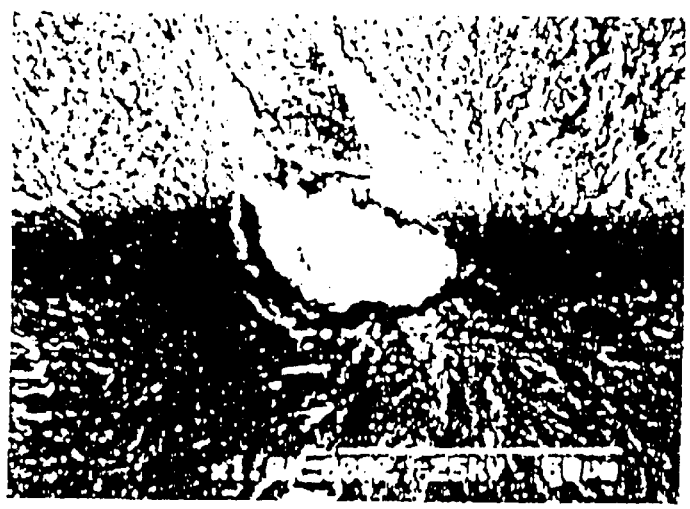

On the other hand, regarding the inclusion-originated internal fracture, if it is assumed that there is hardly any influence of ODA around the inclusion therein, the flaw area becomes, as shown in FIGS. 2(a)–2(c), the flaw area $(area_i)^{1/2}$ which is constituted of only the inclusion and is half of the flaw area that includes the ODA, $(area_h)^{1/2}$. As a result, high tensile strength steel whose tensile strength is substantially the same as that of conventional high tensile strength steel, but whose fatigue limit $\sigma_w$ satisfies the equation $\sigma w=3.58\ (area_i)^{-1/4}$, can be obtained.

Example 2

Next, for the SUP12 steel in which the structure thereof has been made homogeneous and the grains thereof have been made minute, high tensile strength steel was designed by applying the aforementioned method of evaluating a high fatigue strength of the present invention.

Figure 6:
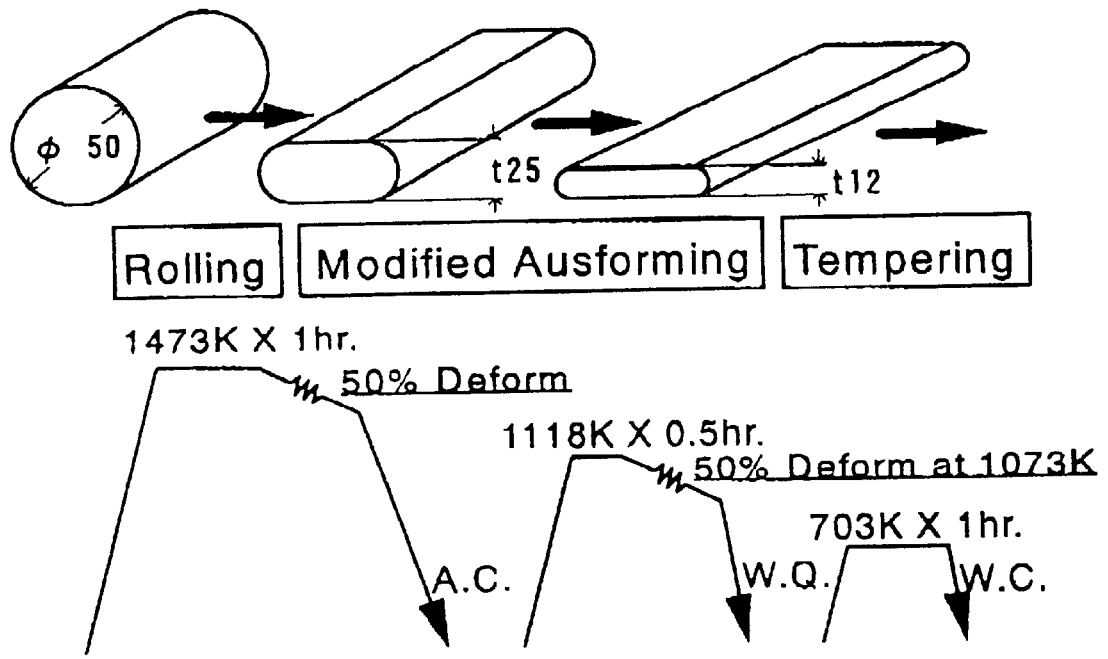
FIG. 6 is a diagram which illustrates a procedure of a thermo-mechanical treatment for creating high fatigue strength steel.

FIG. 6 illustrates a procedure of the heating treatment, which is applied to SUP12 steel so that the structure of the steel is made homogeneous and the grains of the steel are made minute. Specifically, a round rod having a diameter of 50 mm was first held in an electric furnace at 1200° C. for 1 hour as a pre-treatment. Thereafter, the rod was rolled so as to have plate thickness of 25 mm, and then cooled in air. As the modified ausforming process, the rolled plate was held in the electric furnace at 845° C. for 30 minutes, cooled in the air to 800° C., rolled so as to have a plate thickness of 12 mm in two passes, and then cooled again by water. As a tempering process, the steel was held in salt bath at 430° C. for 1 hour and then cooled by water. The Vickers hardness of the steel was 534.

Figure 7:
FIGS. 7(a)–7(b) are optical microscope photographs of inhomogeneous structure.
Figure 7B:
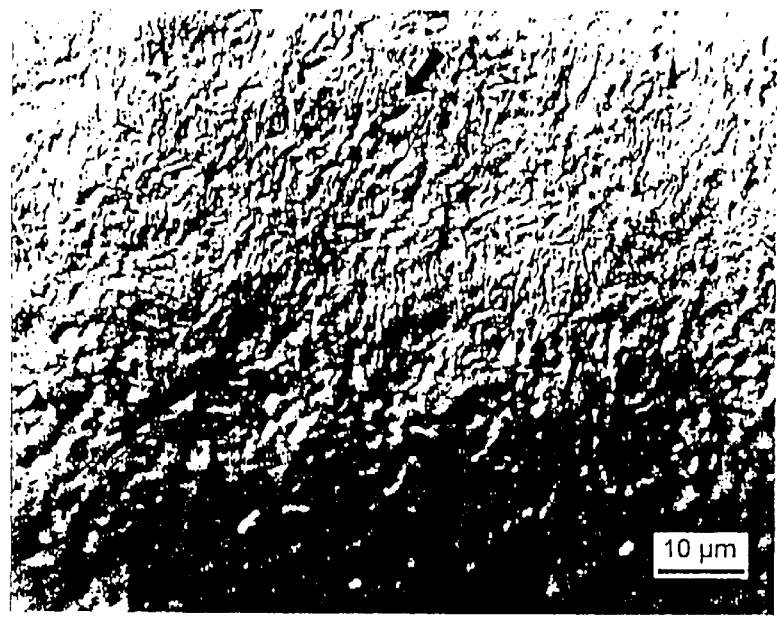
Figure 8:
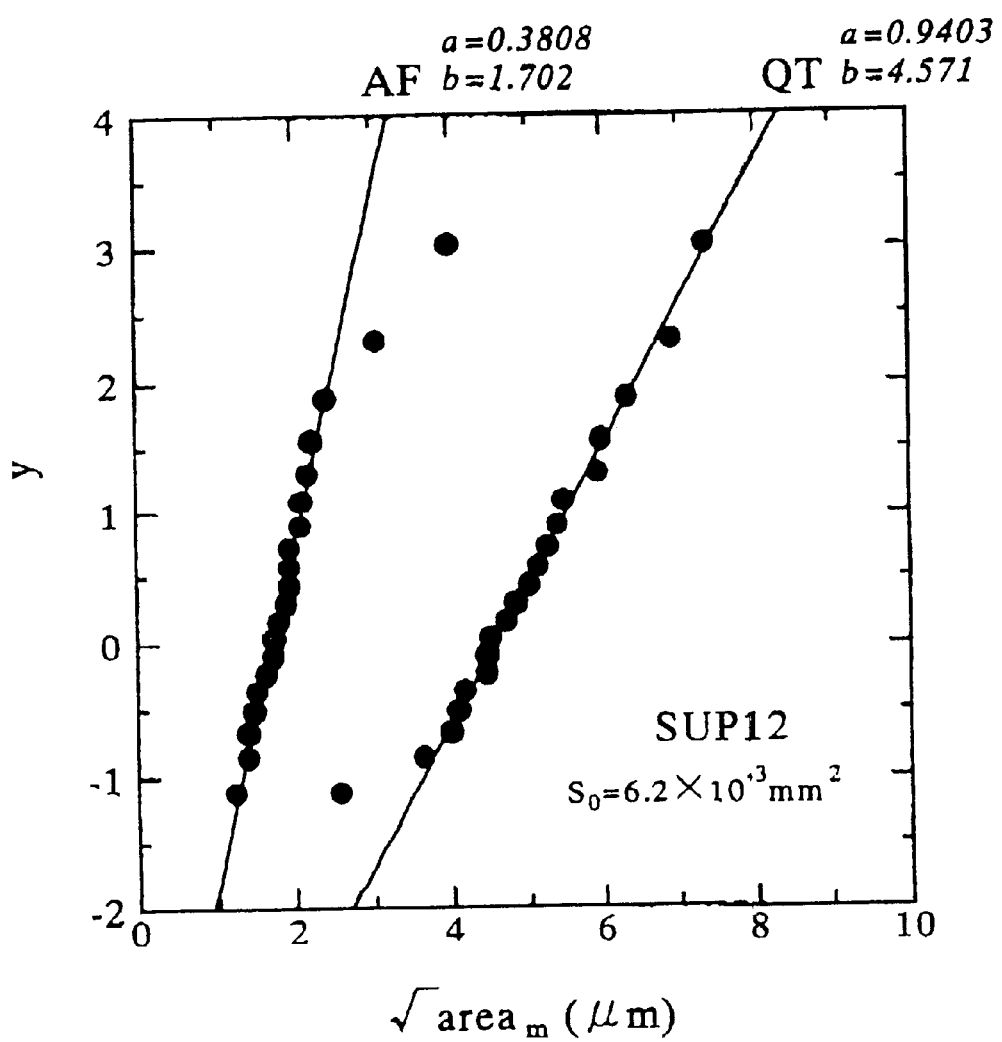
FIG. 8 is a diagram which statistically shows a maximum-minimum range of an inhomogeneous structure area in the embodiment of the present invention.

Examples of the structures of the modified ausform material (the AF material) and the conventionally-quenched-and-tempered material (the QT material) are shown in the photographs of FIGS. 7(a) and 7(b). Each structure includes inhomogeneous structure. The results of statistically analyzing the maximum-minimum range of the area, $(area)^{1/2}$, of the inhomogeneous structure are shown in FIG. 8. The distribution of the maximum-minimum range of the maximum inhomogeneous structure area, $(area_{max,m})^{1/2}$ of the AF material was found within the range defined by the distribution line of the QT material: $(area_{max,\ m})^{1/2}=0.9403y+4.571$ and the line: $(area_{max,\ m})^{1/2}=0$.

Figure 9:
FIGS. 9(a)–9(b) are AFM images of blocks of a tempered martensite structure.
Figure 9B:
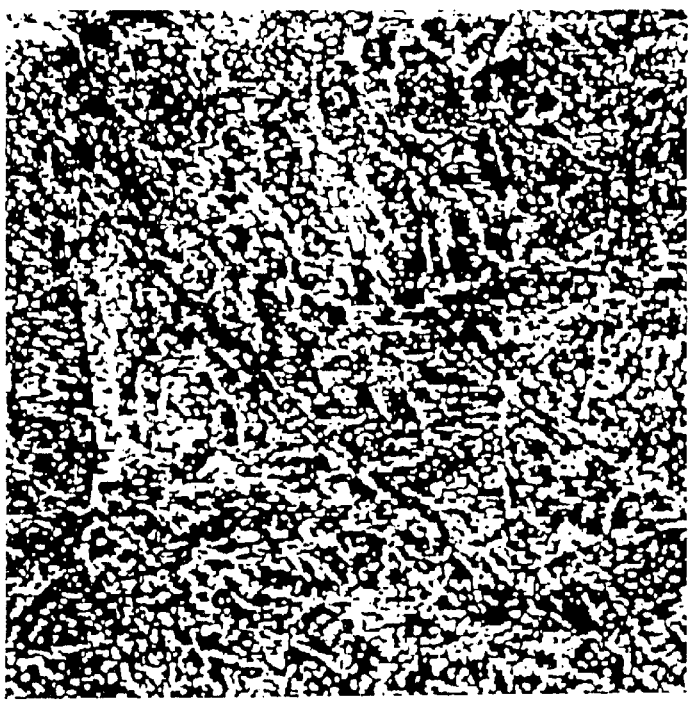
Figure 10:
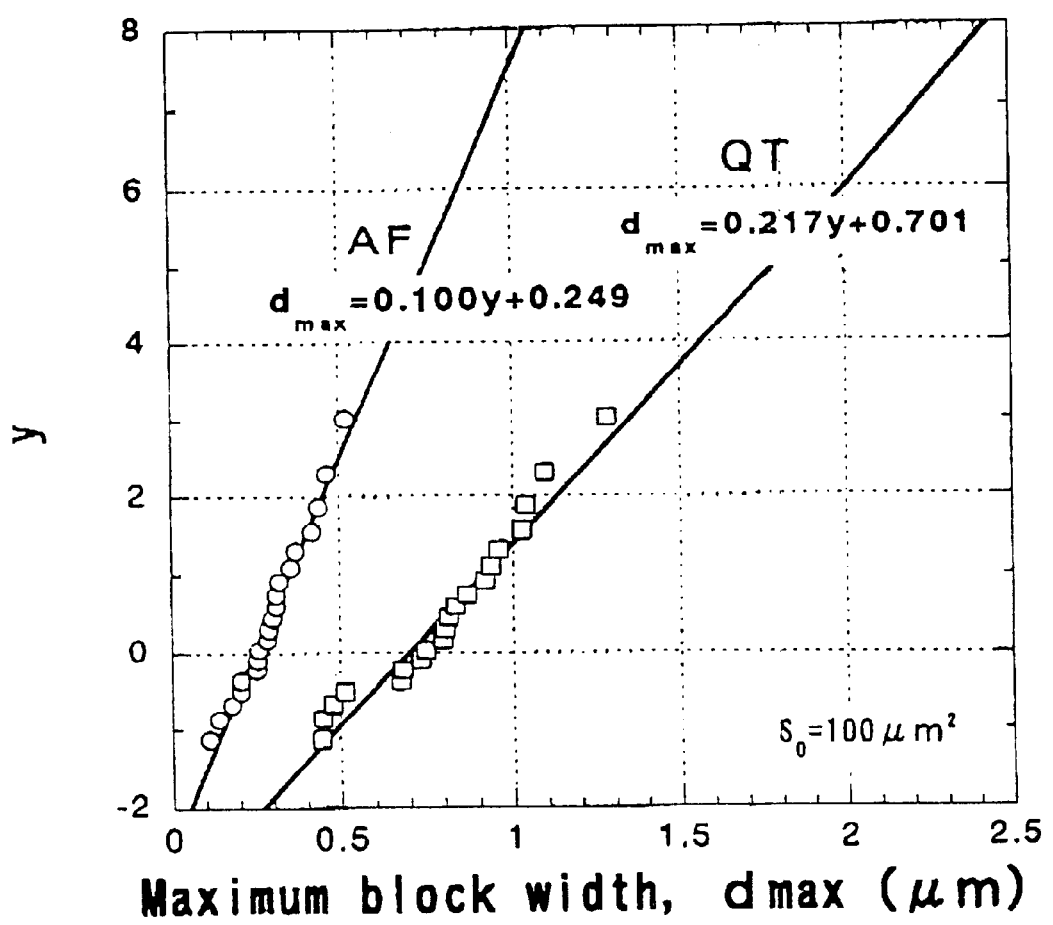
FIG. 10 is a diagram which statistically shows a maximum-minimum range of a maximum block width in the embodiment of the present invention.

Examples of the structure of the tempered martensite of the AF material and the QT material are shown in FIGS. 9(a) and 9(b). When a representative area of the structure is regarded as "block width", the result of statistically analyzing the maximum-minimum range thereof can be plotted as in FIG. 10. The distribution of the maximum-minimum range of the maximum block width $d_{max}$ of the AF material was found within the range defined by the distribution line of the QT material: $d_{max}=0$ and the line: $d_{max}=0.217y+0.701$.

Figure 11:
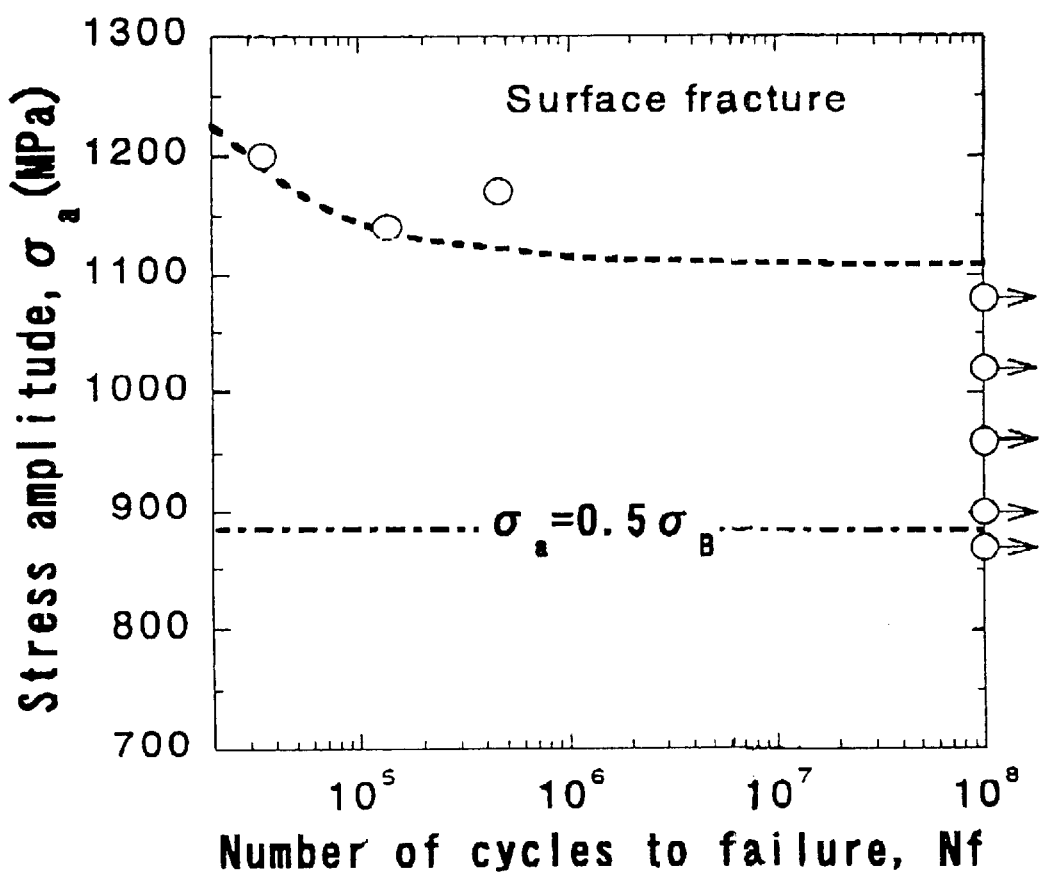
FIG. 11 is a diagram which shows results of a fatigue test of an ausform (AF) steel (size of inclusions were under threshold) in the embodiment of the present invention.

The results, in the case of surface fracture, of the fatigue test of the AF material characteristically having such a structure as described above are shown in FIG. 11. FIG. 11 shows the relationship between the number of cycles to failure Nf and the stress amplitude σa. In FIG. 11, when the flaw area, $(area)^{1/2}$, is no larger than $45.8/\sigma_B^2$, (see equation (b)), the condition that $\sigma_w \geq 0.5\ \sigma_B$, which corresponds to the first aspect of the present invention, is satisfied.

Figure 12:
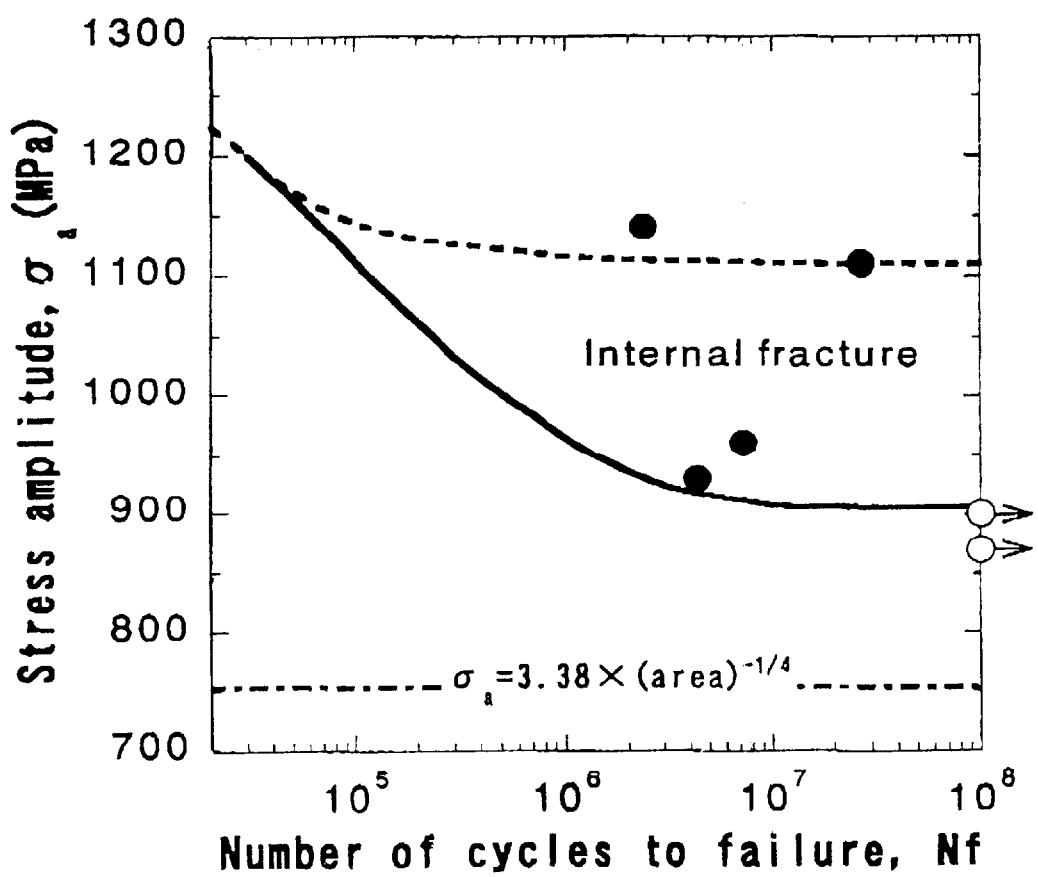
FIG. 12 is a diagram which shows results of a fatigue test of an AF material (size of inclusions were over threshold) in the embodiment of the present invention.

The results, in the case of internal fracture, of the fatigue test of the AF material are shown in FIG. 12. FIG. 12 shows the relationship between the number of cycles to failure Nf and the stress amplitude σa. In FIG. 12, when the flaw area, $(area)^{1/2}$, is larger than $45.8/\sigma_B^2$, (see equation (b)), internal fracture is generated by the inclusion whose flaw area average, $(area)^{1/2}$, is approximately 20 μm (see FIG. 2(c)). However, as there exists no ODA around the inclusion, the condition that $\sigma_w \geq 3.38\ (area_i)^{-1/4}$ (see equation (5)), which corresponds to the second aspect of the present invention, is satisfied.

Example 3

The SUP12 steel produced by the conventional heating treatment was heated to 300° C. in a high vacuum of at least $2\times10^{-6}$ Pa. The Vickers hardness of the steel was 518. The flaw area, $(area)^{1/2}$, was no larger than $45.8/\sigma_B^2$ (see equation (6)), and the condition that $\sigma_w \geq 1.6$ Hv was satisfied.

As described above in detail, the present invention can provide a method of designing high fatigue strength in high tensile strength steel, in which method the relationship between the flaw dimension (area) of ODA and the fatigue strength is considered. The present invention can also provide a high fatigue strength material itself.

What is claimed is:

1. A method of designing a high fatigue strength metal, comprising:

obtaining a value $\sigma_B$, corresponding to a tensile strength of a metal in terms of MPa;

obtaining a value Hv, corresponding to a Vickers hardness of said metal; and estimating a fatigue limit $\sigma_w$, of said metal in terms of MPa to satisfy one of the following equations $$\sigma_w \geq 0.5\ \sigma_B, \qquad (i)$$

and $$\sigma_w \geq 1.6\ Hv \qquad (ii)$$

when a fracture origin is located only at a surface of said metal, and when a square root of a flaw area contained in said metal is not greater than $458/\sigma_B^2$ or $4.47/Hv^2$.

2. The method according to claim 1 wherein said metal comprises steel.

3. The method according to claim 2 wherein said flaw area corresponds to a cross-sectional flaw area.

4. A method of designing a high fatigue strength metal, comprising:

obtaining a value $\sigma_B$ corresponding to a tensile strength of a metal in terms of MPa;

obtaining a value Hv corresponding to a Vickers hardness of said metal;

measuring a flaw area A of an inclusion of said metal when a fracture origin is located inside said metal; and estimating a fatigue limit σw of said metal in terms of Mpa to satisfy the equation $$\sigma_w \geq 3.38\ A^{-\frac{1}{6}}.$$

5. The method according to claim 4 wherein said metal comprises steel.

6. The method according to claim 5, wherein said flaw area A corresponds to a cross-sectional area of said inclusion.

7. A method of evaluating a high tensile strength structure, which method can be used in designing a high fatigue strength metal, said method comprising:

measuring a maximum inhomogeneous elemental area B of a high fatigue strength structure after said high fatigue strength structure has been
  (i) made otherwise homogeneous by limiting the inhomogeneous elemental area, or
  (ii) minuturized by reducing a block width thereof;

when said high fatigue strength structure has been made otherwise homogeneous by limiting the inhomogeneous elemental area, setting a distribution of a maximum-minimum range of said maximum inhomogeneous elemental area B in terms of $\mu$m within a range defined by the lines
  (a) $B^{1/2}=0$, and
  (b) $B^{1/2}=0.9403y+4.571$, wherein y is a standardizing parameter and a test standard area is $6.2\times10^{-9}$ m$^2$; and when said high fatigue strength structure has been miniaturized by reducing a block width thereof, setting a distribution of a maximum-minimum range of the block width d in terms of $\mu$m within a range defined by the lines
  (c) d=0, and
  (d) $d=0.217y+0.701$, wherein y is a standardizing parameter and a test standard area $1.0\times10^{-10}$ m$^2$.

8. The method according to claim 7, wherein said metal comprises steel.

9. A method of producing a high fatigue strength metal, comprising:

designing a high fatigue strength metal by
  (i) obtaining a value $\sigma_B$ corresponding to a tensile strength of a metal in terms of MPa;
  (ii) obtaining a value Hv corresponding to a Vickers hardness of said metal; and
  (iii) estimating a fatigue limit $\sigma_w$ of said metal in terms of MPa to satisfy one of the following equations $$\sigma_w \geq 0.5\ \sigma_B, \qquad (a)$$

and $$\sigma_w \geq 1.6\ Hv \qquad (b)$$

when a fracture origin is located only at a surface of said metal, and when a square root of a flaw area contained in said metal is not greater than $45.8/\sigma_B^2$ or $4.47/Hv^2$; and evaluating a high tensile strength structure by
  (iv) measuring a maximum inhomogeneous elemental area B of a high fatigue strength structure after said high fatigue strength structure has been
    (a) made otherwise homogeneous by limiting the inhomogeneous elemental area, or
    (b) minuturized by reducing a block width thereof;
  (v) when said high fatigue strength has been made otherwise homogeneous by limiting the inhomogeneous elemental area, setting a distribution of a maximum-minimum range of said maximum inhomogeneous elemental area B in terms of $\mu$m within a range defined by the lines
    (1) $B^{1/2}=0$, and
    (2) $B^{1/2}=0.9403y+4.571$, wherein y is a standardizing parameter and a test standard area is $6.2\times10^{-9}$ m$^2$; and
  (vi) when said high fatigue strength structure has been miniaturized by reducing a block width thereof, setting a distribution of a maximum-minimum range of the block width d in terms of $\mu$m within a range defined by the lines
    (3) d=0, and
    (4) $d=0.217y+0.701$, wherein y is a standardizing parameter and a test standard area is $1.0\times10^{-10}$ m$^2$.

10. The method according to claim 9 wherein said metal comprises steel.

11. The method according to claim 10 wherein said flaw area corresponds to a cross-sectional flaw area.

12. A method of producing a high fatigue strength metal, comprising:

designing a high fatigue strength metal by
  (i) obtaining a value $\sigma_B$ corresponding to a tensile strength of a metal in terms of MPa;
  (ii) obtaining a value Hv corresponding to a Vickers hardness of said metal;
  (iii) measuring a flaw area A of an inclusion of said metal when a fracture origin is located inside said metal; and
  (iv) estimating a fatigue limit $\sigma_w$ of said metal in terms of Mpa to satisfy the equation $\sigma_w \geq 3.38\, A^{-1/4}$; and evaluating a high tensile strength structure by
  (v) measuring a maximum inhomogeneous elemental area B of a high fatigue strength structure after said high fatigue strength structure has been
    (a) made otherwise homogeneous by limiting the inhomogeneous elemental area, or
    (b) minuturized by reducing a block width thereof; and
  (vi) when said high fatigue strength has been made otherwise homogeneous by limiting the inhomogeneous elemental area, getting a distribution of a maximum-minimum range of said maximum inhomogeneous elemental area B in terms of $\mu$m within a range defined by the lines
    (1) $B^{1/2}=0$, and
    (2) $B^{1/2}=0.9403y+4.571$, wherein y is a standardizing parameter and a test standard area is $6.2 \times 10^{-9}$ m$^2$; and
  (vii) when said high fatigue strength structure hag been miniaturized by reducing a block width thereof, setting a distribution of a maximum-minimum range of the block width d in terms of $\mu$m within a range defined by the lines
    (3) d=0, and
    (4) d=0.217y+0.701, wherein y is a standardizing parameter and a test standard area is $1.0 \times 10^{-10}$ m$^2$.

13. The method according to claim 12, wherein said metal comprises steel.

14. The method according to claim 13, wherein said flaw area A corresponds to a cross-sectional area of said inclusion.

15. A method of producing a high fatigue strength metal, comprising:
designing a high fatigue strength metal by
  (i) obtaining a value $\sigma_B$ corresponding to a tensile strength of a metal in terms of MPa;
  (ii) obtaining a value Hv corresponding to a Vickers hardness of said metal; and
  (iii) estimating a fatigue limit $\sigma_w$ of said metal in terms of MPa to satisfy one of the following equations $$\sigma_w \geq 0.5\, \sigma_B, \qquad (a)$$

and $$\sigma_w \geq 1.6\, Hv \qquad (b)$$

when a fracture origin is located only at a surface of said metal, and when a square root of a flaw area contained in said metal is not greater than $45.8/\sigma^2_B$ or $4.47/Hv^2$; and subjecting said metal to a heating operation in a vacuum of at least $2 \times 10^{-6}$ Pa to temper said metal.

16. The method according to claim 15 wherein said metal comprises steel.

17. The method according to claim 16, wherein said flaw area corresponds to a cross-sectional flaw area.

18. A high fatigue strength metal produced by:
designing a high fatigue strength metal by
  (i) obtaining a value $\sigma_B$ corresponding to a tensile strength of a metal in terms of MPa;
  (ii) obtaining a value Hv corresponding to a Vickers hardness of said metal; and
  (iii) estimating a fatigue limit $\sigma_w$ of said metal in terms of MPa to satisfy one of the following equations $$\sigma_w \geq 0.5\, \sigma_B, \qquad (a)$$

and $$\sigma_w \geq 1.6\, Hv \qquad (b)$$

when a fracture origin is located only at a surface of said metal, and when a square root of a flaw area contained in said metal is not greater than $45.8/\sigma^2_B$ or $4.47/Hv^2$; and evaluating a high tensile strength structure by
  (iv) measuring a maximum inhomogeneous elemental area B of a high fatigue strength structure after said high fatigue strength structure has been
    (a) made otherwise homogeneous by limiting the inhomogeneous elemental area, or
    (b) minuturized by reducing a block width thereof;
  (v) when said high fatigue strength has been made otherwise homogeneous by limiting the inhomogeneous elemental area, setting a distribution of a maximum-minimum range of said maximum inhomogeneous elemental area B in terms of $\mu$m within a range defined by the lines
    (1) $B^{1/2}=0$, and
    (2) $B^{1/2}=0.9403y+4.571$, wherein y is a standardizing parameter and a test standard area is $6.2 \times 10^{-9}$ m$^2$; and
  (vi) when said high fatigue strength structure has been miniaturized by reducing a block width thereof, setting a distribution of a maximum-minimum range of the block width d in terms of $\mu$m within a range defined by the lines
    (3) d=0, and
    (4) d=0.217y+0.701, wherein y is a standardizing parameter and a test standard area is $1.0 \times 10^{-10}$ m$^2$.

19. The high fatigue strength material according to claim 18, wherein said metal comprises steel.

20. The high fatigue strength metal according to claim 19, wherein said flaw area corresponds to a cross-sectional flaw area.

21. A high fatigue strength metal produced by:
designing a high fatigue strength metal by
  (i) obtaining a value $\sigma_B$ corresponding to a tensile strength of a metal in terms of MPa;
  (ii) obtaining a value Hv corresponding to a Vickers hardness of said metal;
  (iii) measuring a flaw area A of an inclusion of said metal when fracture origin is located inside said metal; and
  (iv) estimating a fatigue limit $\sigma_w$ of said metal in terms of Mpa to satisfy the equation $\sigma_w \geq 3.38\, A^{-1/4}$; and evaluating a high tensile strength structure by
  (v) measuring a maximum inhomogeneous elemental area B of a high fatigue strength structure after said high fatigue strength structure has been
    (a) made otherwise homogeneous by limiting the inhomogeneous elemental area, or (b) minuturized by reducing a block width thereof; and (vi) when said high fatigue strength has been made otherwise homogeneous by limiting the inhomogeneous elemental area, setting a distribution of a maximum-minimum range of said maximum inhomogeneous elemental area B in terms of $\mu$m within a range defined by the lines
   (1) $B^{1/2}=0$, and
   (2) $B^{1/2}=0.9403y+4.571$, wherein y is a standardizing parameter and a test standard area is $6.2\times10^{-9}$ m²; and (vii) when said high fatigue strength has been miniturized by reducing a block width thereof, setting a distribution of a maximum-minimum range of the block width d in terms of $\mu$m within a range defined by the lines
   (3) d=0, and
   (4) d=0.217y+0.701, wherein y is a standardizing parameter and a test standard area is $1.0\times10^{-10}$ m².

22. The high fatigue strength metal according to claim 15 wherein said metal comprises steel.

23. The high fatigue strength metal according to claim 22, wherein said flaw area A corresponds to a cross-sectional area of said inclusion.

* * * * *